(12) United States Patent
Vishwakarma et al.

(10) Patent No.: US 9,776,989 B2
(45) Date of Patent: Oct. 3, 2017

(54) CHROMONE ALKALOID DYSOLINE FOR THE TREATMENT OF CANCER AND INFLAMMATORY DISORDERS

(71) Applicant: Council of Scientific & Industrial Research, New Dehli (IN)

(72) Inventors: Ram Asrey Vishwakarma, Jammu (IN); Shreyans Kumar Jain, Jammu (IN); Sandip Bibishan Bharate, Jammu (IN); Abid Hamid Dar, Jammu (IN); Anamika Khajuria, Jammu (IN); Samdarshi Meena, Jammu (IN); Sunil Kumar Bhola, Jammu (IN); Asif Khurshid Qazi, Jammu (IN); Aashiq Hussain, Jammu (IN); Tabasum Sidi, Jammu (IN); Shaanker Ramanan Uma, Bangalore (IN); Gudasalamani Ravikanth, Bangalore (IN); Ramesh Vasudeva, Dhaward Sirsi (IN); Kumara Patel Mohana, Bangalore (IN); Kotiganahalli Narayanagowda Ganeshaiah, Bangalore (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 14/783,878

(22) PCT Filed: Mar. 31, 2014

(86) PCT No.: PCT/IN2014/000201
§ 371 (c)(1),
(2) Date: Oct. 12, 2015

(87) PCT Pub. No.: WO2014/167580
PCT Pub. Date: Oct. 16, 2014

(65) Prior Publication Data
US 2016/0046611 A1 Feb. 18, 2016

(30) Foreign Application Priority Data
Apr. 10, 2013 (IN) .......................... 1077/DEL/2013

(51) Int. Cl.
*C07D 405/04* (2006.01)
*C07D 311/24* (2006.01)

(52) U.S. Cl.
CPC .......... *C07D 405/04* (2013.01); *C07D 311/24* (2013.01)

(58) Field of Classification Search
None
See application file for complete search history.

(56) References Cited

PUBLICATIONS

International Search Report and Written Opinion for International Patent Application No. PCT/IN2014/000201, dated Jul. 25, 2014.
Jain, et, al.; Isolation and biological evaluation of chromone alkaloid dysoline, a new regioisomer of rohitukine from Dysoxylum binectariferum; Tetrahedron Letters; Oct. 28, 2013; pp. 7140-7143; vol. 54, No. 52; Elsevier Ltd.
Mohanakumara, et al.; Dysoxylum binectariferum Hook.f (Meliaceae), a rich source of rohitukine; Fitoterapia; Aug. 15, 2009; pp. 145-148; vol. 81, No. 2; Elsevier B.V.

*Primary Examiner* — Timothy R Rozof
(74) *Attorney, Agent, or Firm* — McDonald Hopkins LLC

(57) ABSTRACT

The present invention relates to novel chromone alkaloid of formula 1 isolated from the plant *Dysoxylum binectariferum*. The compound 5,7-dihydroxy-6-(3-hydroxy-1-methylpiperidin-4-yl)-2-methyl-4H-chromen-4-one, is found to be a potential inhibitor of cell growth and proliferation and also inhibits production of pro-inflammatory cytokines. The formulations of this particular compound can be used for treatment of cancer and inflammation.

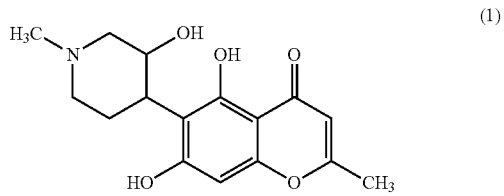

(1)

14 Claims, 3 Drawing Sheets

Fig. 1

HMBC and COSY correlations

| Sr. No. | Carbon | $^{13}$C (δ ppm) | $^1$H (δ ppm) |
|---|---|---|---|
| 1 | C-2 | 169.59 | - |
| 2 | C-3 | 109.01 | 6.13 (s, 1H) |
| 3 | C-4 | 184.16 | - |
| 4 | C-4a | 105.09 | - |
| 5 | C-5 | 161.22 | - |
| 6 | C-6 | 111.62 | - |
| 7 | C-7 | 158.56 | - |
| 8 | C-8 | 95.82 | 6.74 (s, 1H) |
| 9 | C-8a | 164.23 | - |
| 10 | C-9 | 20.32 | 2.11 (s,3H) |
| 11 | C-1' | 36.28 | 3.98-3.95 (m, 1H) |
| 12 | C-2' | 68.34 | 4.68 (brs, 1H) |
| 13 | C-3' | 61.68 | 3.72-3.58 (m, 2H) |
| 15 | C-5' | 59.73 | 5'a: 3.43-3.40 (m, 1H) |
|  |  |  | 5'b: 3.89-3.86 (m, 1H) |
| 16 | C-6' | 22.98 | 6'a: 1.87-1.85 (m, 1H) |
|  |  |  | 6'b: 3.17-3.13 (m, 1H) |
| 17 | N-CH$_3$ | 44.26 | 3.15 (s, 3H) |

CHROMONE ALKALOID DYSOLINE FOR THE TREATMENT OF CANCER AND INFLAMMATORY DISORDERS

This application is a 35 U.S.C. 371 national stage filing and claims priority to PCT Application No. PCT/IN2014/000201, entitled "Novel Chromone Alkaloid Dysoline for the Treatment of Cancer and Inflammatory Disorders" filed on Mar. 31, 2014, which claims priority to Indian Application No. 1077/DEL/2013 filed on Apr. 10, 2013, both of which are incorporated by reference herein in their entirety.

FIELD OF THE INVENTION

The present invention relates to novel chromone alkaloid compound, Dysoline, which is isolated from the plant *Dysoxylum binectariferum*. The present invention particularly relates to 5,7-dihydroxy-6-(3-hydroxy-1-methylpiperidin-4-yl)-2-methyl-4H-chromen-4-one, having anticancer and anti-inflammatory activity. The present invention also relates to a process for its isolation and purification. The present invention relates to a compound that is a potential inhibitor of cell growth and proliferation and also inhibits production of pro-inflammatory cytokines. More particularly the present invention relates to the use of these isolated compounds as pharmacologically active compounds for the treatment of cancer and inflammatory disorders.

BACKGROUND OF THE INVENTION

Chromone and flavonoid alkaloids are an important group of natural products possessing promising medicinal properties. Large number of naturally occurring chromone and flavonoid alkaloids are reported in the literature, varying in type of nitrogen system and its position of attachment on chromone/flavonoid nucleus. Their natural occurrence and biological activities have been recently reviewed by Khadem and Manes (Khadem, S. et. al. *Molecules* 2012, 17, 191). This class of alkaloids also led to discovery of potent anticancer molecule flavopiridol which received orphan drug status for treatment of Chronic myelogenous leukemia (reviewed in: Jain, S. K. et. al. *Mini-Rev. Med. Chem.* 2012, 12, 632). Rohitukine, 5,7-dihydroxy-2-methyl-8-[4-(3-hydroxy-1-methyl)-piperidinyl]-4H-1-benzopyran-4-one, is a chromone alkaloid originally isolated from leaves and stems bark of *Amoora rohituka* Roxb. (Meliaceae) (Harmon, A. D. et. al. *Tetrahedron Lett.* 1979, 8, 721) and then isolated as major component from the stem bark of *Dysoxylum binectariferum* Roxb. (Meliaceae) (Yang, D. H. et. al. *J. Asian Nat. Prod. Res.* 2004, 6, 233). Rohitukine was also isolated from barks of *Schumanniophyton magnificum* and *S. problematicum* (Rubiaceae) (Houghton, P. J. *Planta Med.* 1988, 54, 239; Houghton, P. J. et. al. *Phytochem. Anal.* 1993, 4, 9). Rohitukine showed moderate cytotoxicity against human HL-60 promyelocytic leukemia and HCT-116 colon cancer cells. Several more complex cytotoxic chromone alkaloids have been isolated from leaves and bark of *Dysoxylum acutangulum* of Meliaceae (Ismail, I. S. et. al. *J. Nat. Prod.* 2009, 72, 1879). Medicinal chemistry efforts around these nature-derived chromone alkaloid led to discovery of two promising clinical candidates for treatment of cancer viz. flavopiridol of Sanofi-aventis and P-276-00 of Piramal life sciences. (Naik, R. G. *Tetrahedron* 1988, 44, 2081; U.S. Pat. No. 4,900,727). With respect to bioactivities, many of these flavonoid and chromone alkaloids have been discovered through bioassay-guided chemical investigations, suggesting that they have significant potential for drug discovery.

*Dysoxylum binectariferum* is one of the plant in India of the Meliaceae family which mainly occurs in Western ghats of India. Rohitukine was found to be a major constituent of its bark extract, which is responsible for immunomodulatory activity (Mohanakumara, P. et al., *Fitoterapia* 2010, 81, 145-148; Naik, R. G. et al. *Tetrahedron* 1988, 44, 2081).

OBJECTIVES OF THE INVENTION

The main object of the present invention is to provide a novel compound known as Dysoline of formula 1

Formula 1

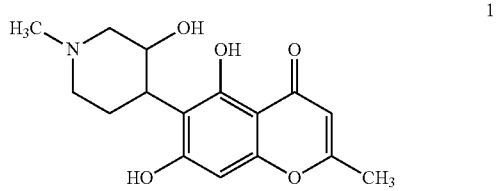

isolated from the plant *Dysoxylum binectariferum*.

Another object of the present invention is to provide 5,7-dihydroxy-6-(3-hydroxy-1-methylpiperidin-4-yl)-2-methyl-4H-chromen-4-one(dysoline) having anticancer and anti-inflammatory activity Still another object of the present invention is to provide a process for isolation and purification of dysoline compound.

Still another object of the present invention is to provide a Dysoline compound that is a potent inhibitor of cell growth and proliferation and also inhibits production of pro-inflammatory cytokines.

Yet another object of the present invention is to use the compound for the treatment of cancer and inflammatory disorders.

SUMMARY OF THE INVENTION

Accordingly the present invention provides a compound of formula 1 or a pharmaceutically acceptable salt thereof, Formula 1

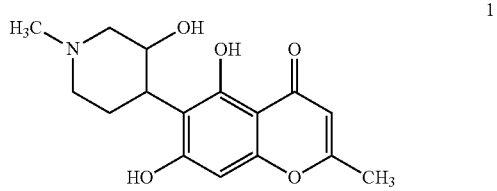

In an embodiment of the invention, the compound is 5,7-dihydroxy-6-(3-hydroxy-1-methylpiperidin-4-yl)-2-methyl-4H-chromen-4-one.

In an embodiment of the invention, the compound is isolated from *Dysoxylum binectariferum*.

In another embodiment of the invention, the compound exhibits anti-inflammatory and anticancer activity.

In yet another embodiment of the invention, the compound inhibits cytokines TNF-α and IL-6, at a concentration in the range of 0.01 μM to 100 μM.

In a further embodiment of the invention, the compound exhibits activity against Colo 205, HCT116 (Colon); HT1080 (Fibrosarcoma); NCIH322, A549 (Lung) and MOLT-4, HL-60 (Leukemia) at $IC_{50}$ values in the range of 0.2 µM to >10 µM.

In one more embodiment of the invention, the compound shows growth inhibition activity against leukemia and fibrosarcoma cell lines where $IC_{50}$ values is in the range of 0.21 to 10 µM.

A process for the preparation of compound of formula 1, wherein said process comprises of following steps:
a) powdering of plant material obtained from *Dysoxylum binectariferum* followed by extraction with alcohol to obtain an extract;
b) evaporating the solvent of the extract obtained from step (a) in vacuo rotavapor to obtain a residue and then partitioning with hexane and water to obtain a water soluble material;
c) acidifying the water soluble material obtained from step b) to a pH in the range of 2 to 5 followed by filtration to obtain a filtrate;
d) basifying the filtrate obtained from step c) to a pH in the range of 8 to 11 followed by filtration to obtain a filtrate,
e) loading the filtrate obtained from step d) over HP20 resin and eluting with water and methanol to obtain a fraction containing rohitukine
f) subjecting remaining fraction of step e) to silica gel column chromatography and eluting with $CHCl_3$-MeOH or $CH_2Cl_2$-MeOH or EtOAc-MeOH in the range of 5% to 10% and further purifying on Sephadex gel to yield compound of formula 1.

In an embodiment of the invention, the plant material used is bark.

In another embodiment of the invention, the resin used in step e) is HP-20 resin (dianion).

In one more embodiment of the invention, yield of the compound of formula 1 obtained is 0.05%.

In yet another embodiment of the invention, the acid is selected from the group consisting of hydrochloric acid and sulfuric acid.

In another embodiment of the invention, the base is selected from the group consisting of sodium bicarbonate, ammonia, calcium hydroxide and sodium hydroxide.

BRIEF DESCRIPTION OF THE DRAWINGS

FIG. 1 is a diagram illustrating the key HMBC/COSY correlations and $^1H/^{13}C$ NMR assignments for compound 1.

FIG. 2 B is a diagram illustrating the overlay CD spectrum of dysoline and rohitukine to determine the relative stereochemistry of dysoline.

Table 1 provides the information on anticancer activity of dysoline (1) and rohitukine in panel of cancer cell lines Table 2 provides the information on percentage inhibition of cytokine production by dysoline (1)

DETAILED DESCRIPTION OF THE INVENTION

The present invention reports new chromone alkaloid dysoline (compound of formula 1) having anticancer and antiinflammatory activity, isolated from *Dysoxylum binectariferum*.

The molecular formula of the compound is $C_{16}H_{19}NO_5$ and it has molecular weight of 305.32 g/mol. The chemical structure of dysoline (1) is shown below:

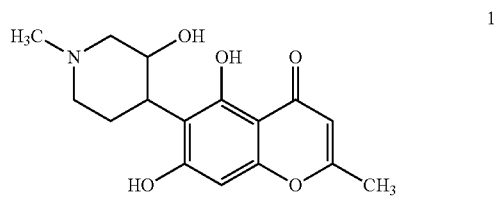

Figure 2:
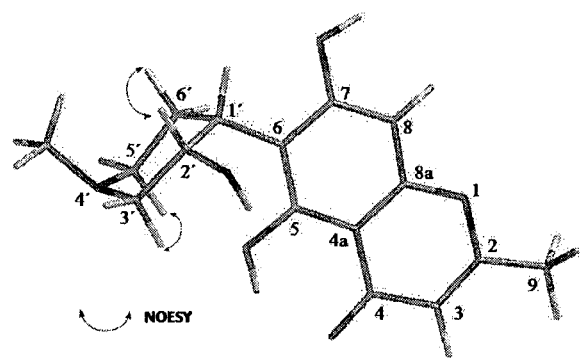
FIG. 2 A is a diagram illustrating the key NOESY correlations of dysoline.
Figure 2:
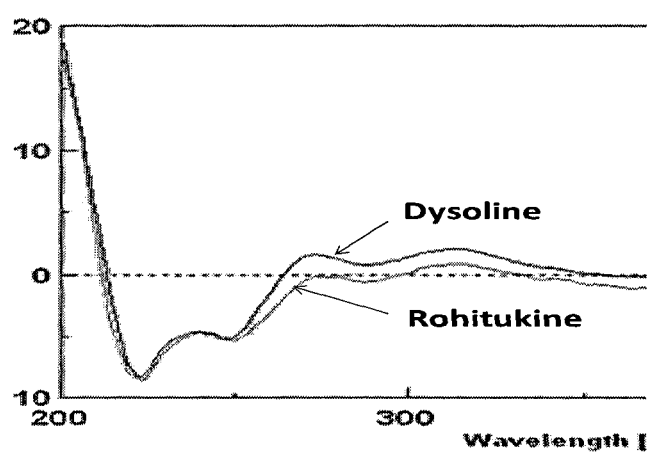

The present invention relates to relates to new chromone alkaloid dysoline (5,7-dihydroxy-6-(3-hydroxy-1-methylpiperidin-4-yl)-2-methyl-4H-chromen-4-one; 1) as anticancer and antiinflammatory agent. This alkaloid has been isolated from barks of *D. binectariferum* using cold maceration in 70% ethanol. Compound is characterized using extensive spectroscopic data. Compound 1 showed molecular mass similar to rohitukine (mol. wt.=305), however TLC retention factor ($R_f$) and melting point were different. The molecular formula was established as $C_{16}H_{19}NO_5$ using HR-ESIMS analysis. IR absorptions implied the presence of hydroxy (3399 $cm^{-1}$) and carbonyl (1654 $cm^{-1}$) functionalities. Further similar patterns in $^1H$, $^{13}C$ and DEPT NMR to that of rohitukine indicated its structural closeness to rohitukine. Dragendroff positive test indicated presence of alkaloid skeleton which was further identified as N-methylpiperidine ring system based on $^1H$-$^1H$ COSY spectrum. Further based on HSQC and HMBC correlations, structure was identified as 5,7-dihydroxy-6-(3-hydroxy-1-methylpiperidin-4-yl)-2-methyl-4H-chromen-4-one (1). HMBC correlations and $^1H/^{13}C$ NMR assignments are shown in FIG. 1. The relative configuration of 1 was determined by using NOESY and CD spectra (FIG. 2). In the NOESY spectrum of compound 1, two important correlation: H-2' with H-6' and H-3' with H-5' were observed, which indicated chair conformation of the piperidine ring (FIG. 2*a*). Further, the absolute stereochemistry of compound 1 was assigned by applying the exciton chirality method (Harada, N. and Nakanishi, K. *J. Am. Chem. Soc.* 1969, 91, 3989). The CD spectra of compound 1 was found to be identical to rohitukine (FIG. 2*b*) which has absolute stereochemistry as 1'R, 2'S. Thus the absolute stereochemistry in the dysoline (1) was identified as 1'R, 2'S (similar to that of rohitukine).

Figure 3:
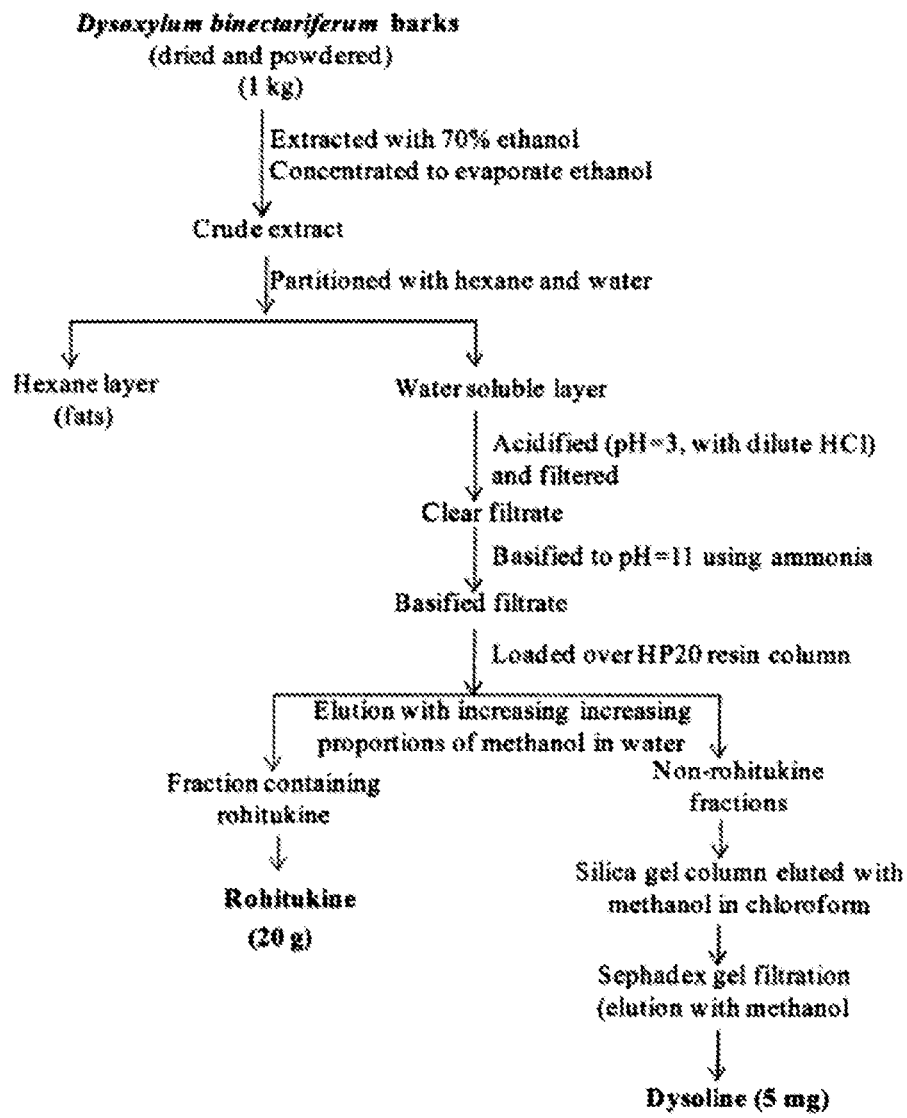

FIG. 3 is a flow chart showing how *dysoxylum binectariferum* barks may be extracted via a separation with ethanol and hexane and water. The hexane layer contains fats and is separated from the water soluble layer, which is subsequently acidified, filtered, basified, and filtered. After elution with increasing proportions of methanol in water, a rohitukine fraction is obtained. The non-rohitukine fraction is eluted in a silica gel column with methanol in chloroform, followed by a sephadex gel filtration (eluted with methanol), to produce dysoline.

Anticancer activity of dysoline (1) along with rohitukine was evaluated using MTT cell viability assay on eight cancer cell lines viz. Colo205 (colon), HCT116 (colon), HT1080 (fibrosarcoma), NCIH322 (lung), A549 (lung), Molt-4 (leukemia) and HL60 (leukemia).

Results are shown in Table 1. $IC_{50}$ values of compound 1 in these cell lines was found to be >10, >10, 0.21, >10, >10, >10 and 10 µM respectively. Results indicated that dysoline (1) possess potent activity against fibrosarcoma cell line HT1080 with $IC_{50}$ value of 0.21 µM, indicating its potential role specifically in treatment of fibrosarcoma cancer. However, rohitukine showed $IC_{50}$<10 µM in HT1080 cells, indicating better potency of dysoline compared to rohitukine in this cell line (Cancer, 1974, 33, 1027). The cells were originated from the European Collection of Cell Cultures (ECACC, UK) and purchased through Sigma-Aldrich India.

Anti-inflammatory activity of dysoline (1) was evaluated by inhibiting production of pro-inflammatory cytokines such as tumor necrosis factor-alpha (TNF-α) and interleukin-6 (IL-6). Dysoline displayed 53 and 83% inhibition of TNF-α and IL-6 production at 1 µM. The TNF-α inhibition activity of dysoline was compared with rohitukine. It was observed that, at 1 µM, rohitukine showed 32% inhibition of TNF-α production whereas 53% inhibition by dysoline, indicating the better activity of dysoline compared to rohitukine.

In a second aspect of the invention, a new compound presented for treating or preventing cancer by identifying a patient suffering from or at a risk of developing a cancer or inflammatory disorder and administering to the patient a therapeutically-effective amount of a compound represented by the formula 1, or a salt, ester or prodrug thereof.

In one embodiment, the compound may be useful for the treatment of fibrosarcoma.

Two asymmetric centers exist in the compound of the present invention. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention can exist in unsolvated as well as solvated forms with pharmaceutically acceptable solvents such as water, ethanol, and the like.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diasteroisomers differ not only in the way they rotate plane polarized light, but also their physical properties. The term "optical isomer" comprises more particularly the enantiomers and the diastereoisomers, in pure form or in the form of a mixture.

The term "cancer" as used herein refers to any disease, disorder, condition, or symptom characterized by the uncontrolled growth of abnormal cells in the body.

The phrase "therapeutically effective" is intended to qualify the amount of active ingredients used in the treatment of a disease or disorder. This amount will achieve the goal of reducing or eliminating the disease or disorder.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

The compound of the invention can exist as therapeutically acceptable salt. The present invention includes compound listed above in the form of salt, in particular acid addition salt. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The present invention relates to discovery of new chromone alkaloid 5,7-dihydroxy-8-(3-hydroxy-1-methylpiperidin-4-yl)-4H-chromen-4-one (dysoline, 1) that shows promising anticancer activity. The inhibitory properties of the compounds of the invention can therefore be used to treat or prevent diseases, disorders, conditions, or symptoms in a patient (e.g. human) that involve, directly, or indirectly, uncontrolled and abnormal growth of tissues/cells of any part of the body. New compound 5,7-dihydroxy-8-(3-hydroxy-1-methylpiperidin-4-yl)-4H-chromen-4-one (dysoline, 1) is presented and defined by structural formula 1.

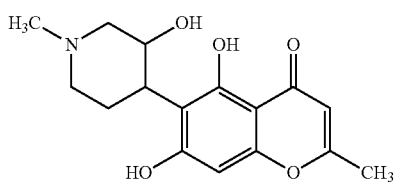

5,7-Dihydroxy-8-(3-hydroxy-1-methylpiperidin-4-yl)-4H-chromen-4-one

Cancer.

Compound of the invention can be used to treat a patient (e.g. a human) at a risk of developing or already suffering from a cancer.

Inflammatory Diseases.

One or more compounds of the invention can be used to treat a patient (e.g. a human) at a risk of developing or already suffering from a inflammatory disease, such as rheumatoid arthritis, inflammatory bowel disease, psoriasis, asthma and chronic obstructive pulmonary disorder.

Methods of Prevention and Treatment.

Compound of the invention can be used to treat a patient (e.g. a human) that suffers from or is at a risk of suffering from a disease, disorder, condition, or symptom described herein. Compound of the invention can be used alone or in combination with other agents and compounds in methods of treating or preventing cancer. Each such treatment described above includes the step of administering to a patient in need thereof a therapeutically effective amount of the compound of the invention described herein to delay, reduce or prevent such a disease, disorder, condition, or symptom. Besides being useful for human treatment, the compound of the present invention is also useful for the treatment of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

Compound administration and formulation.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Carriers and polymers such as microcrystalline cellulose, dicalcium phosphate, polyvinyl pyrrolidone, hydroxypropyl methyl cellulose, ethyl cellulose, chitosan, gelatin, eudragit, etc can be used.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Compound of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Such agents include magnesium stearate, sodium lauryl sulfate, carboxy methyl cellulose, tween 80, span 80, etc. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Compound of the invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration. Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. Via the topical route, the pharmaceutical composition according to the invention may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion Thus, in another aspect, methods for treating diseases, disorders, conditions, or symptoms in a patient (e.g., a human or animal) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

In a related aspect, therapeutic compositions having novel compound of the invention described herein can be administered in combination with one or more additional agents for the treatment of any of the diseases, disorders, conditions, or symptoms described herein.

It is understood that the foregoing examples are merely illustrative of the present invention. Certain modifications of the articles and/or methods employed may be made and still achieve the objectives of the invention. Such modifications are contemplated as within the scope of the claimed invention.

The following examples are given by way of illustration and therefore, should not be considered to limit the scope of the present invention.

Example 1

Isolation of Dysoline from Bark of *Dysoxylum Binectariferum*

*Dysoxylum binectariferum* tree samples were collected from three different sites (namely Jog, Kathagal and Jamboti) of the central Western Ghats of Karnataka, India. Each tree was given a unique ID and labeled with either paint or tag. Voucher specimens (COF\DBT\WG-185-1-36) for each of the sample tree collected was deposited at the herbarium of the College of Forestry, Sirsi (University of Agricultural Sciences, Dharwad, India). Bark of this plant was separated and powdered. The powdered material (1 kg) was extracted with 70% ethanol (3 L×2) using cold maceration method. Ethanol was evaporated on vacuo rotavapor. The crude extract was defatted by partitioning with hexane and water. The water-soluble material was acidified (pH=3, with dilute HCl) and filtered. Clear filtrate was then basified to pH=11 using ammonia and loaded over HP20 resin to adsorb organic material, which was eluted with water and methanol (with increasing proportion of methanol). A major compound showing positive test for alkaloid, was isolated (20 g, 2%) which after spectral characterization was identified as rohitukine (Mohanakumara, P. et al., *Fitoterapia* 2010, 81, 145). Remaining alkaloid positive fraction was combined and subjected to silica gel column chromatography (#100-200) and eluted with $CHCl_3$-MeOH (85:15) to yield alkaloid rich mixture, which finally after purification on Sephadex gel yielded cream colored solid (5 mg, 0.05% of dry plant material). 5,7-dihydroxy-6-(3-hydroxy-1-methylpiperidin-4-yl)-2-methyl-4H-chromen-4-one (1): Cream colored solid; m.p. 310-315° C.; $^1H$ NMR (500 MHz, pyridine-$d_5$): ☐ 6.74 (s, 1H), 6.13 (s, 1H), 4.68 (brs, 1H), 3.98-3.95 (m, 1H), 3.89-3.86 (m, 1H), 3.72-3.58 (m, 2H), 3.43-3.40 (m, 1H), 3.17-3.13 (m, 1H), 3.15 (s, 3H), 2.11 (s, 3H), 1.87-1.85 (m, 1H); $^{13}C$ NMR (125 MHz, methanol-$d_4$, ppm): δ 184.16, 169.59, 164.23, 161.22, 158.56, 111.62, 109.01, 105.09, 95.82, 68.34, 61.68, 56.73, 44.26, 36.98, 22.98, 20.32; IR (KBr): $v_{max}$ 3399, 2924, 2350, 1659, 1556, 1417, 1271, 1186 $cm^{-1}$; MS (ESI-MS): m/z 306.1339 $(M+H)^+$; HRMS: m/z 306.1320 $(M+H)^+$ calcd. for $C_{16}H_{20}NO_5$ (306.1336).

Example 2

Anticancer Activity Against Panel of Cell Lines

The cell were originated from The European Collection of Cell Cultures (ECACC, UK) and purchased through Sigma-Aldrich India.

The MTT assay was used to assess the effect of the test molecules on cell viability. Cell viability on eight cell lines viz. Colo205 (colon), HCT116 (colon), HT1080 (fibrosarcoma), NCIH322 (lung), A549 (lung), Molt-4 (leukemia) and HL60 (leukemia) was investigated. In each well of a 96-well plate, $3\times10^3$ cells were grown in 100 µL of medium. After 24 h, each test molecules were added to achieve a final concentration of 10 to 0.01 µmol/L, respectively. After 48 h of treatment, 20 µL of 2.5 mg/mL MTT (Organics Research, Inc.) solution in phosphate buffer saline was added to each well. After 48 h, supernatant was removed and formazan crystals were dissolved in 200 µL of DMSO. Absorbance was then measured at 570 nm using an absorbance plate reader (Bio-Rad Microplate Reader). Data are expressed as the percentage of viable cells in treated relative to non-treated conditions. Each experiment was repeated thrice and data was expressed as mean±SD of three independent experiments (*Mol. Cancer Ther.* 2010, 9, 358-368).

TABLE 1

Anticancer activity of dysoline (1) and rohitukine in panel of cancer cell lines

| Cell line | Rohitukine $IC_{50}$ (µM) | Dysoline (1) $IC_{50}$ (µM) |
|---|---|---|
| Colo205 (Colon) | >10 | >10 |
| HCT116 (Colon) | >10 | >10 |
| HT1080 (fibrosarcoma) | >10 | 0.21 |
| NCIH322 (lung) | >10 | >10 |
| A549 (lung) | >10 | >10 |
| MOLT-4 (leukemia) | >10 | >10 |
| HL-60 (leukemia) | 10 | 10 |

Example 3

Effect of Dysoline (1) on Production of Pro-Inflammatory Cytokines TNF-α and IL-6

Splenocytes of male Balb/c mice were seeded into three to four wells of a 96-well flat-bottom microtiter plate (Nunc) at $2\times10^6$ cells/ml. Cells were incubated with different concentrations of dysoline (0.01 µM-100 µM) along with Con A (2.5 µg/well) or LPS (1 µg/ml) for 72 h at 37° C. with 5% $CO_2$ in $CO_2$ incubator. The culture supernatants were harvested and the measurement of cytokines (TNF-α and IL-6) in the culture supernatants was carried out using commercial kits as per manufacturer's instructions by using ELISA kits (R&D, USA) (*Life Sci.* 2007, 80, 1525-1538; *J. Immunol. Methods* 1983, 65, 55-63). Dysoline (1) showed inhibition of TNF-α and IL-6 production at low micromolar to nanomolar concentrations as shown in Table 2.

TABLE 2

Percentage inhibition of cytokine production by dysoline (1) and rohitukine

| Concn (µM) | dysoline (1) | | rohitukine | |
|---|---|---|---|---|
| | TNF-α | IL-6 | TNF-α | IL-6 |
| 100 | 56 | 99 | 47 | 89 |
| 10 | 54 | 89 | 32 | 88 |
| 1 | 53 | 83 | 28 | 80 |
| 0.1 | 47 | 83 | 22 | 30 |
| 0.01 | 28 | 72 | 18 | 10 |

ADVANTAGES OF THE INVENTION

The compound so isolated, Dysoline is a new chemical entity.

Dysoline can be utilized as a promising anticancer activity against fibrosarcoma cell line HT1080. Dysoline showed inhibition of production of pro-inflammatory cytokines.

The compound has good water solubility and is stable.

We claim:

1. A composition of matter comprising solvated and unsolvated forms of a compound of formula 1 or a pharmaceutically acceptable salt thereof, Formula 1

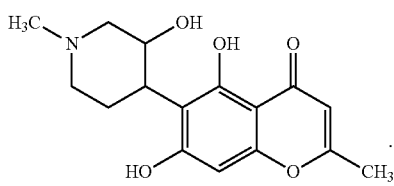

2. The composition of matter as claimed in claim 1, wherein the compound is 5,7-dihydroxy-6-(3-hydroxy-1-methylpiperidin-4-yl)-2-methyl-4H-chromen-4-one.

3. The composition of matter as claimed in claim 1, wherein the compound is isolated from *Dysoxylum binectariferum*.

4. The composition of matter as claimed in claim 1, wherein the compound is for use in a method of treating inflammation and cancer.

5. The composition of matter as claimed in claim 4, wherein the compound is for use in inhibiting cytokines TNF-α and IL-6, at a concentration in the range of 0.01 μM to 100 μM.

6. The composition of matter as claimed in claim 4, wherein the compound is for use in exhibiting activity against Colo 205, HCT116 (Colon); HT1080 (Fibrosarcoma); NCIH322, A549 (Lung) and MOLT-4, HL-60 (Leukemia) at $IC_{50}$ values in the range of 0.2 μM to >10 μM.

7. The composition of matter as claimed in claim 4, wherein the compound is for use in showing growth inhibition activity against MOLT-4, HL-60 (leukemia) cell lines when $IC_{50}$ value is >10 μM.

8. The composition of matter as claimed in claim 4, wherein the compound is for use in showing growth inhibition activity against fibrosarcoma cell lines when $IC_{50}$ value is 0.21 μM.

9. A process for the preparation of compound as claimed in claim 1, wherein, said process comprises of following steps:—
a) powdering of plant material obtained from *Dysoxylum binectariferum*, followed by extraction with alcohol to obtain an extract;
b) evaporating the solvent of the extract obtained from step (a) in vacuo rotavapor to obtain a residue and then partitioning with hexane and water to obtain a water soluble material;
c) acidifying the water soluble material obtained from step b) to a pH in the range of 2 to 5, followed by filtration to obtain a filtrate;
d) basifying the filtrate obtained from step c) to a pH in the range of 8 to 11, followed by filtration to obtain a filtrate;
e) loading the filtrate obtained from step d) over HP20 resin and eluting with water and methanol to obtain a fraction containing rohitukine;
f) subjecting remaining fraction of step e) to silica gel column chromatography and eluting with $CHCl_3$-MeOH or $CH_2Cl_2$-MeOH or EtOAc-MeOH in the range of 5% to 10% and further purifying on Sephadex gel to yield compound of formula 1.

10. The process as claimed in claim 9, wherein the plant material used in step a) is bark.

11. The process as claimed in claim 9, wherein yield of the compound of formula 1 obtained is 0.05%.

12. The process as claimed in claim 9, wherein the acid of step c is selected from the group consisting of hydrochloric acid and sulfuric acid.

13. The process as claimed in claim 9, wherein the base of step d is selected from the group consisting of sodium bicarbonate, ammonia, calcium hydroxide and sodium hydroxide.

14. The composition of matter as claimed in claim 2, wherein the compound is isolated from *Dysoxylum binectariferum*.

* * * * *